United States Patent
Agarwal et al.

(10) Patent No.: US 11,883,228 B2
(45) Date of Patent: Jan. 30, 2024

(54) SMART STETHOSCOPES

(71) Applicant: Cambridge Enterprise Limited, Cambridgeshire (GB)

(72) Inventors: Anurag Agarwal, Cambridgeshire (GB); Edmund Kay, Cambridgeshire (GB); Andrew McDonald, Cambridgeshire (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 813 days.

(21) Appl. No.: 16/978,932

(22) PCT Filed: Feb. 20, 2019

(86) PCT No.: PCT/GB2019/050461
§ 371 (c)(1),
(2) Date: Sep. 8, 2020

(87) PCT Pub. No.: WO2019/171021
PCT Pub. Date: Sep. 12, 2019

(65) Prior Publication Data
US 2021/0169442 A1 Jun. 10, 2021

(30) Foreign Application Priority Data
Mar. 9, 2018 (GB) ...................... 1803805

(51) Int. Cl.
*A61B 7/04* (2006.01)
*A61B 5/00* (2006.01)
(52) U.S. Cl.
CPC .............. *A61B 7/04* (2013.01); *A61B 5/7264* (2013.01)

(58) Field of Classification Search
CPC ........ A61B 7/04; A61B 5/7264; A61B 5/7267
See application file for complete search history.

(56) References Cited

U.S. PATENT DOCUMENTS 6,498,854 B1 12/2002 Smith
8,855,757 B2 10/2014 Kapoor
(Continued)

FOREIGN PATENT DOCUMENTS

WO 2015715904 A1 11/2015

OTHER PUBLICATIONS

Olivera et al, "On modifying the temporal modelling of HSMMS for pediatric heart sound segentation", 2017 IEEE Workshop on Signal Processing Systems, Lorient, pp. 1-6.

*Primary Examiner* — Shirley X Jian
(74) *Attorney, Agent, or Firm* — TAROLLI, SUNDHEIM, COVELL & TUMMINO L.L.P.

(57) ABSTRACT

An electronic stethoscope system comprising a device to capture an acoustic heart signal from a patient and a neural network to classify the data into heart sound categories to provide time series sound category data comprising, for each of a succession of time intervals, category probability data representing a probability of the acoustic signal falling into each of the categories. The stethoscope also includes one or more heart state models each having a sequence of heart cardiac cycle states, a system to fit the time series sound category data to the models and determine timing data for the sequence of heart states and a confidence value for the model fit, and an output to output one or both of a model fit indication dependent upon the confidence value and an indication of the timing data.

21 Claims, 7 Drawing Sheets

(56) References Cited

U.S. PATENT DOCUMENTS

| | | | |
|---|---|---|---|
| 9,320,442 B2 | 4/2016 | Kapoor | |
| 9,492,138 B2 | 11/2016 | Kapoor | |
| 10,966,681 B2* | 4/2021 | Datta | A61B 7/04 |
| 11,373,757 B2* | 6/2022 | Das | A61B 7/04 |
| 11,432,753 B2* | 9/2022 | Alam | G16H 50/20 |
| 2003/0093003 A1* | 5/2003 | Watrous | A61B 7/00 |
| | | | 600/528 |
| 2007/0276270 A1* | 11/2007 | Tran | A61B 5/0022 |
| | | | 600/508 |
| 2008/0013747 A1* | 1/2008 | Tran | A61B 5/0295 |
| | | | 381/67 |
| 2010/0106038 A1* | 4/2010 | Schmidt | A61B 7/04 |
| | | | 600/528 |
| 2010/0249629 A1 | 9/2010 | Schmidt et al. | |
| 2011/0190665 A1 | 8/2011 | Bedingham et al. | |
| 2013/0150754 A1 | 6/2013 | Rogers et al. | |
| 2014/0343446 A1* | 11/2014 | Hallberg | A61B 7/04 |
| | | | 600/528 |
| 2015/0201272 A1 | 7/2015 | Wong | |
| 2019/0008475 A1* | 1/2019 | Datta | A61B 5/7267 |
| 2019/0192110 A1* | 6/2019 | Parvaneh | A61B 7/00 |
| 2020/0046244 A1* | 2/2020 | Alam | G06N 3/045 |
| 2021/0169442 A1* | 6/2021 | Agarwal | A61B 5/7264 |

* cited by examiner

SMART STETHOSCOPES

RELATED APPLICATIONS

The present invention is a U.S. National Stage under 35 USC 371 patent application, claiming priority to Serial No. PCT/GB2019/050461, filed on 20 Feb. 2019; which claims priority of GB 1803805.9, filed on 9 Mar. 2018, the entirety of both of which are incorporated herein by reference.

FIELD

This specification relates to electronic stethoscope systems and methods.

BACKGROUND

An electronic stethoscope can capture sound, digitise the captured sound, and provide the result to a computer. An intelligent stethoscope, able to detect heart conditions such as murmurs and the like, could make a valuable contribution to the medical community, in particular in the developing world. However there are currently few stethoscopes on the market that are capable of offering this kind of analysis.

Background prior art can be found in: US2015/0201272; US2011/0190665; US2013/0150754; U.S. Pat. Nos. 6,498,854; 9,320,442; 8,855,757; 9,492,138; WO2015/175904; US2003/0093003; US2010/0249629; and Olivera et al, "On modifying the temporal modelling of HSMMS for pediatric heart sound segentation", 2017 IEEE Workshop on Signal Processing Systems, Lorient, pp 1-6.

A paper authored by the inventors, not prior art in the USA, entitled "*DropConnected neural networks trained on time-frequency and inter-beat features for classifying heart sounds*", Physiol Meas. 2017 Jul. 31; 38(8):1645-1657, describes a technique in which an acoustic heart signal is segmented into S1, systole, S2 and diastole phases. Using this segmentation time-frequency features are extracted and fed into a neural network to distinguish between normal and abnormal sounds. However this approach is prone to errors, particularly when strong murmur signals are present.

SUMMARY

In one aspect there is therefore provided a method, and corresponding system, for processing acoustic heart signal data. The method may comprise capturing time series acoustic heart signal data from a patient, the time series acoustic heart signal data representing the sound of the patient's heart. The method/system may further involve classifying the time series acoustic heart signal data, for example using a neural network, into a plurality of heart sound categories to provide time series sound category data wherein the time series sound category data comprises, for each of a plurality of time intervals, category probability data representing a probability of the acoustic heart signal for the time interval falling into each of the heart sound categories.

The method/system may further involve fitting the time series sound category data to one or more heart state models each having a sequence of heart states. In implementations the heart states have associated heart sounds corresponding to the heart sound categories. In implementations the heart states may have adjustable durations, and thus the fitting may determine timings of the sequence of states.

Probabilities of the associated heart sounds for fitting the time series sound category data may be given by the category probability data.

The method/system may further comprise determining a confidence value for the model fit and/or data identifying timings of the sequence of states. The method may still further comprise outputting one or both of a model fit indication dependent upon the confidence value, and the data identifying timings of the sequence of states.

The sequence of heart, more specifically cardiac cycle, states may be defined by the model. The states may have adjustable durations in the model. Fitting the time series sound category data to the heart state model may comprise determining timings of the sequence of states, for example by determining which heart state is most likely present for each time interval. For example the method/system may identify when one state ends and a next state starts to identify state transition times. Thus fitting the time series sound category data to the heart state model may determine a most likely state for each of the time intervals; this may further involve determining a most likely sequence of states, including their timings, for example using a Viterbi or similar algorithm.

The confidence value for the model fit may be determined from the timings of the sequence of states and their corresponding category probability data. The model fit indication may comprise a binary indication that there is a model fit, or otherwise. Where the observations are fitted to two models the model fit indication may indicate the best fit. Where the captured data is of insufficient quality for a good fit, for example where the confidence value is beneath a threshold, this may also be indicated. In some implementations a degree of goodness of fit may be indicated.

Some implementations of the method/system provide advantages including fast and accurate processing of acoustic heart data (phonocardiograms), for example to identify an abnormality in the heart sound. This may be used to facilitate identification of a heart condition, for example by indicating which patients should be prioritised for closer investigation for triage purposes. Some implementations of the system may be particularly advantageous in developing countries. The method/system is sufficiently economical in battery/processing power to be physically implementable as part of a stethoscope, although in some other implementations the processing may be partly or wholly implemented remotely, for example in the cloud. The system may be used in both primary and secondary care, and also has applications in fitness monitoring and the like.

Implementations of the technique work much better than the approach described in the inventors' previous paper (ibid). In broad terms in the previous work the acoustic and segmentation (heart) states were the same. By contrast as described herein separately identifying the acoustic states and then using these in a sequence model to identify heart states facilitates correctly determining the heart states, and at the same time can determine whether or not the phonocardiogram is normal. The techniques can also provide a confidence level for this determination. Thus an indication of whether or not the phonocardiogram is normal may be provided by the heart state sequence model rather than by a second stage neural network.

To expand upon this, where the acoustic states and the segmentation states are the same (e.g. S1, systole, S2, and diastole) it can be difficult to acoustically distinguish between S1/S2, and systole/diastole, which limits performance. Thus, in implementations the acoustic states comprise 3 different sounds i.e. the heart sound categories comprise at least major heart sound, no sound, and murmur.

These are then fed into the heart state model, rather than using a 1:1 mapping between acoustic and segmentation states.

In some implementations, after capture of the time series acoustic heart signal data this is converted to a time series of acoustic feature data, for example representing energy in different frequency bands of the signal. The acoustic features may comprise features for a range of frequencies including frequencies from <50 Hz, for example down to 25 Hz, and/or to >200 Hz, for example up to 400 Hz. In some heart diseases sounds at certain frequencies are not present, and thus capturing information from a range of frequencies reduces the risk of not capturing relevant data.

The method/system may classify the acoustic feature/signal data with a neural network into a plurality of categories to produce time series sound category data which is a time series of, for each category, the probability of the category. The categories may be categories of heart sound type such as major heart sound, no sound, and murmur. Thus the neural network output data may comprise acoustic heart sound categories.

The method/system may then postulate a model of the heart. This may have a sequence of heart states, which may correspond to states of the heart whilst beating. The heart states may comprise S1, systole, S2 and diastole heart states. Although S1 and S2 are often referred to as heart sounds here they represent the corresponding heart states for the S1 and S2 heart sounds, and relate to the operation of valves within the heart. As described later the cardiac cycle sequence model states may be states of a Duration-dependent Hidden Markov Model.

There may be two models, e.g. two Markov chains, one for a normal, one for an abnormal heart, with different sequences of associated heart sounds. The first model may represent a normal phonocardiogram and the second mode may represent an abnormal phonocardiogram e.g. with a systolic or diastolic murmur. This can facilitate determination of whether a murmur is present.

In implementations the durations of the states are not fixed, they are defined by probability distributions. Some of the probability distributions may be fixed a priori, some may be dependent upon heart rate—that is some of the states may have a duration which has a probability distribution which is independent of heart rate; others may depend on heart rate. Techniques for estimation of a heart rate are described later.

In implementations each state is associated with one of the sound categories. That is, the probability of a state at particular time is given by the probability of the sound category. These probabilities are output from the neural network. The heart sound categories may comprise categories of sound "heard", that is identified, by the neural network. The heart states may be states of a sequential model of heart states, for example S1, systole, S2, diastole, with associated heart sounds. The sequential model may assume the systolic and/or diastolic phases are normal or contain murmurs.

A modelling process uses these probabilities to fit the model(s) of the heart sound to the observations i.e. to the observed acoustic heart signal data. That is, the probabilities of the categories are combined with the probabilities defined in the model to segment the observed acoustic heart signal data into a (most likely) series of model states, where the segmentation defines the sequence of cardiac states, for example by defining when the heart changes from one state to the next according to the model. Thus a result of the fitting process may be to assign a most likely heart state to each time of the time series. The sequence of states is fixed for a model; the duration of the states is allowed to vary.

When used by the model, the probability of a state at particular time is converted to the probability of an observation given the state, using Bayes theorem. An observation may be an observation of the acoustic heart signal at a particular time and/or data derived from this, such as one or more spectral features of the acoustic heart signal.

The heart state model may be a Hidden Markov Model (HMM), in particular a Duration-dependent Hidden Markov Model (DHMM). However other sequential models may alternatively be employed. As previously mentioned, the most likely sequence of states may be determined using a Viterbi algorithm.

Once the model has been fit to the data by determining when the states occur, that is by assigning a most likely heart state to each time of the time series, a degree of confidence in the model fit can be determined. For example for each time of the time series the probability of the assigned heart state may be determined from the probability of the corresponding sound category, as provided by the neural network. These probabilities may be combined to determine a probability or confidence for the model fit. The probabilities may be combined, for example, by multiplication, or by addition if log probabilities are employed, or in some other way. The confidence of the model fit may be used to identify whether the sequence of states postulated by the model is a good fit to the observations.

For example the probability or confidence for the model fit may be compared to a threshold value to determine whether the observations are well represented by the model. The model may be a model of a normal heart sound state sequence or a model of an abnormal heart sound state sequence. Thus the model fit may be used to identify whether the observations correspond to a normal heart or to an abnormal heart with a heart condition.

In some implementations both normal and abnormal heart models are fitted to the observations and the model with the best fit used to identify whether the observations correspond to a normal or to an abnormal heart sound state sequence. The abnormal heart sound state sequence may represent a heart with a systolic murmur, diastolic murmur, or other abnormality, particularly abnormalities which are repeated every heartbeat. Where the probability or confidence of the model fit is below a quality threshold the observations may be identified as of poor quality and no normal/abnormal determination attempted.

Thus in broad terms, using the posterior probabilities from the neural network as an indicator of the confidence of segmentation facilitates determining whether or not a murmur is present (as described above, using two models e.g. two Markov chains), and/or can also provide an indication as to whether or not the signal e.g. recorded signal, is of an acceptable quality or not.

In some implementations the techniques described herein determine two sets of states, acoustic states which categorise the sounds captured from the heart, such as major heart sound, no sound, and murmur, and heart states which use the determined acoustic states, and more particularly their probabilities, to determine a sequence of states for the heart. The sequence of states for the heart may be labelled so as to correspond with states typically identified by a clinician, such as S1, systole, S2 and diastole. The segmentation of the heart states may be used to determine a timing of these states, for example their durations and/or when one ends and another begins.

There may be multiple different abnormal models, each corresponding to a different underlying heart condition. For example heart murmurs can occur at different points in the cardiac cycle, and these may have different state sequence models, more particularly state sequence models with different with associated heart sounds.

Distinct from this there are different categories into which the heart sounds may be classified for use in fitting a model. Thus in some implementations the categories used comprise no sound, a heart murmur, and a major heart sound, but additional or alternative categories may be employed, for example to detect clicks, rubs, or other sounds.

The probability or confidence of the fit to three or more different models may be combined to identify a heart condition not represented by either model individually. For example where the models represent normal, abnormal type A and abnormal type B conditions, where abnormal type A and abnormal type B are identified as the two most likely models a type C heart condition may be identified. For example where a systolic murmur and a diastolic murmur are identified as the most likely models then a continuous murmur may be identified.

The sequence of heart states in the model may be a defined sequence. The defined sequence may be defined probabilistically, for example using state transition probability values defining probabilities of transitioning between states. The defined sequence may be enforced, for example by setting transition probabilities equal to 1 or 0. In some implementations the duration dependence may be relaxed, for example by employing duration distributions with greater variance, or a model which does not rely on modelling duration.

Arrhythmia may manifest itself in different ways, for example as one or more of missed beats, extra beats, and a seemingly random non-periodic succession of beats. Reducing the enforced periodicity of the model may facilitate detecting arrhythmia. However the model may segment the captured data into heart states without requiring the data to be periodic. Then missed/extra beats may be detected, for example, by determining whether the durations of any states are significantly different from their mean duration.

The method/system may also determine a measure of an intensity of a heart sound comprising a murmur, for example according to the Levine grading scale. This may comprise determining, for each of a plurality of times during the murmur, a set coefficients characterising the time series acoustic heart signal data over a plurality of frequency bands. The coefficients may be MFCC (mel-frequency cepstral coefficients) coefficients. The set of coefficients for each time may then be mapped to a murmur intensity value, for example according to a learned regression. The murmur intensity values may then be combined, for example by averaging, to determine the measure of the intensity of the murmur.

A heart rate for use in the above described method/system may be determined from the time series acoustic heart signal data. This may then be used to adapt the probability distributions for the durations of one or more of the states to the determined heart rate by, for example, determining the mean of one or more of the durations using the heart rate. The heart rate may be determined by an autocorrelation operation. The autocorrelation operation may be performed on the time series acoustic heart signal data; or on the time series of acoustic feature data; or on the time series sound category data, more particularly on the category probability data for one or more categories. A result of the autocorrelation operation may be combined with, e.g. multiplied by, a prior probability distribution of the heart rate for improved reliability, for example a prior Gaussian probability distribution.

In another aspect there is provided a method, and corresponding system, for processing an acoustic heart signal. The method comprises capturing an acoustic heart signal from a patient, for example using a microphone in an associated chestpiece, and processing the acoustic heart signal to provide an acoustic data sequence. The acoustic data sequence comprises a sequence of data elements representing the acoustic heart signal, for example digitised frequency component and/or amplitude values of the acoustic heart signal. The method may comprise classifying the sequence of data elements using a neural network to provide a sequence of acoustic data category classifications and associated probabilities. Each acoustic data category classification may, for example, classify one or more of the data elements into one or more of a plurality of acoustic heart data categories each with an associated probability.

The method/system may further involve processing the sequence of acoustic data category classifications and associated probabilities using one or more sequence models. Each sequence model may represent the likelihood of a sequence of heart sounds represented by the acoustic data category classifications and associated probabilities. The processing may identify a most likely sequence of the heart sounds. The method may then output data identifying the most likely sequence of the heart sounds. This may represent a determination of whether or not a likely heart disorder has been identified.

Two models may be employed, one to represent abnormal heart sound and another normal heart sound. Multiple models may be employed to differentiate between multiple different types of abnormal heart sound. Thus the method may involve selecting a most likely model from the plurality of sequence models to identify the most likely sequence of the heart sounds. With a single model, for example of an abnormal heart sound, the output data may identify whether or not the abnormal heart sound is likely, for example by comparison with a threshold. The output data may, at its simplest, comprise a single bit of information such as an optical indicator showing red or green, for example to represent an abnormal or normal heart sound.

In some implementations each sequence model may represent a postulated succession of heart states, each heart state having one or more associated acoustic heart data categories. For example the acoustic heart data categories may comprise no sound, a heart murmur, and a major heart sound, where a major heart sound may comprise one or both of the first (S1) and second (S2) heart sounds. More categories may optionally be employed. The neural network may provide a probability value for each of these categories, for example for each data element of the sequence, which typically corresponds to each time interval of a succession of time intervals. A sequence model may comprise a defined sequence of heart states. The probability of each heart sound in the sequence may be provided to the sequence model from the neural network. Thus the sequence model may be provided with a probability value for each heart state of the sequence it defines. These probabilities may then be combined to determine a probability value for the sequence.

In some implementations a Hidden Markov Model (HMM) may be employed for this purpose in which case the probability values may correspond to the state probability values of the HMM. The HMM may be a hidden semi-Markov model, sometimes also referred to as duration-dependent hidden Markov model, that is where the state probability values depend upon the elapsed time since the start of the state.

In some other implementations a suitable sequence model may comprise a Gaussian Mixture Model (GMM) or a Recurrent Neural Network (RNN).

The neural network may comprise any neural network suitable for processing a sequence of data elements. Thus one option is to use a recurrent neural network such as a LSTM (Long Short-Term Memory) or GRU (Gated Recurrent Unit) network. However a feedforward network such as a convolutional neural network may additionally or alternatively be used to process the sequence of data elements.

The method may include determining a confidence level for the most likely sequence of the heart sounds, that is for the most likely sequence model. This may be derived from the probability of the model given the observations (acoustic heart data). The output data may include, explicitly or implicitly, an indication of whether a threshold confidence level is met by the most likely sequence. For example, if the threshold confidence level is not met the method may simply fail to provide an output. Alternatively a separate indication may be provided that a good quality signal has been obtained, and/or that a reliable determination has been made.

In some implementations of the method an estimate of the heart rate is derived from the heart signal and used by the sequence model(s) to provide a priori information regarding the expected duration of the heart data categories. This information may thus be used to adjust the probabilities for the acoustic data classifications, in particular in a time-dependent manner. In this way the likelihood of transitions between states of the sequence model can be adjusted according to elapsed time since the start of a state. Some states of the sequence model may have a duration modelled by a fixed distribution, for example S1 and/or S2 heart states. Other states of the sequence model may have a duration modelled by a distribution dependent upon the heart rate, for example systole and/or diastole heart states. The distributions of the durations may be taken into account by the sequence model.

In some implementations a heart rate may be estimated from the acoustic heart signal, for example from an envelope of this signal. However in other implementations the heart rate may be estimated from the acoustic heart data categories and their associated probabilities. This may be done, for example, by performing an autocorrelation on a time series of one or more of these probabilities.

A sequence model may segment an acoustic heart signal or phonocardiogram (PCG) into segments. In general these segments will correspond to the states derived from classifying the heart signal, although there need not be a one-to-one correspondence. The sequence model takes the probabilities from classifying the sequence of data elements from the heart signal and may include a priori information built into an expected sequence to which the sequence model attempts to match the probabilities. However as part of fitting a sequence model to the probabilities the model may also output data defining the model's segmentation of the heart signal. The model may also output likelihood data identifying when one or more segments is absent and/or a sequence model may itself correspond to include missing or extra states of the heart signal. Thus the method may be extended to detect arrhythmia, such as missed beats and extra beats.

Where multiple sequence models are used the models may correspond to one or more of: no murmur; systolic murmur; and diastolic murmur. As previously described, a sequence model may provide a probability or confidence level of a particular sequence model fitting the observed signal. The output probabilities of multiple models may be combined to identify further heart disorders. For example where systolic murmur and diastolic murmur models represent the two highest probabilities the system/method may output data identifying that a continuous murmur may be present.

In some implementations processing the acoustic heart signal to provide an acoustic data sequence may comprise determining spectral or frequency-domain data for the acoustic heart signal at each of a succession of time intervals to determine the sequence of data elements representing the acoustic heart signal. The spectral or frequency-domain data may comprise data representing an amplitude or energy of the acoustic heart signal in each of a plurality of frequency bands. For example the acoustic heart signal data from the patient may be bandpass filtered and the envelope taken. In some other implementations the acoustic heart data may be processed directly by the neural network after digitization, that is without conversion into a frequency-domain representation.

In another aspect a method of processing acoustic heart signal data comprises capturing time series acoustic heart signal data from a patient, the time series acoustic heart signal data representing the sound of the patient's heart. The method may then comprise extracting acoustic features from the time series acoustic heart signal data to provide time series acoustic feature data. The method may then comprise classifying the time series acoustic feature data using each of at least two heart models, a first heart model representing a normal heart and a second heart model represents a heart with a heart murmur. The method may then comprise determining which of the first model and the second model best fits the acoustic heart signal data. The method may then comprise outputting data indicating whether or not the patient's heart has a heart murmur when the second heart model fits the acoustic heart signal data better than the first model.

The classifying may comprise determining first and second label sequences using the first and second heart models respectively. Each label sequence may comprise, for each of a plurality of time instances, at least a most likely label for the acoustic heart signal data at the time instance and a corresponding label probability. Determining which of the first model and the second model best fits the acoustic heart signal data may comprise combining the label probabilities for each sequence to determine a respective confidence value for each of the first and second label sequences, and comparing the confidence values for the sequences.

The first heart model may be a model in which the first label sequence comprises labels for sounds associated with a normal cardiac cycle S1, systole, S2, diastole. The second heart model may be a model in which the second label sequence comprises labels for sounds associated with a cardiac cycle with a murmur. For example the first heart model may have labels for S1, systole, S2, and diastole; and the second heart model may have labels for S1, systolic murmur, S2, and diastole.

The classifying may use a recurrent neural network (RNN) for each of the heart models. More particularly the set of labels available to the RNN for classifying the type of heart sounds may comprise a superset of the labels used for the first and second heart models. Then when implementing the first heart model the RNN may be constrained only to use labels belonging to the first heart model (i.e. no murmur label), and when implementing the second heart model the RNN may be constrained only to use labels belonging to the second heart model (e.g. no systole label). The neural network may be constrained in this way by disregarding the corresponding label output and selecting from the remaining labels when classifying a type of heart sound. The RNN may be, for example a network of gated recurrent units; the RNN may be unidirectional or bidirectional.

The invention further provides processor control code to implement the above-described systems and methods, for example on a general purpose computer system, or on a mobile device, or on a digital signal processor (DSP). The code is provided on a non-transitory physical data carrier such as a disk, CD- or DVD-ROM, programmed memory such as non-volatile memory (eg Flash) or read-only memory (Firmware). Code and/or data to implement embodiments of the invention may comprise source, object or executable code in a conventional programming language (interpreted or compiled) such as C, or assembly code, or code for a hardware description language. As the skilled person will appreciate such code and/or data may be distributed between a plurality of coupled components in communication with one another.

There is also provided an electronic stethoscope system including such a non-transitory physical data carrier.

Thus in another aspect there is provided an electronic stethoscope system, the system comprising: an acoustic signal capture device to capture time series acoustic heart signal data from a patient; a neural network to classify the time series acoustic heart signal data into a plurality of heart sound categories to provide time series sound category data, wherein the time series sound category data comprises, for each of a succession of time intervals, category probability data representing a probability of the acoustic heart signal for the time interval falling into each of the heart sound categories; one or more heart state models each having a sequence of heart states; a system to fit the time series sound category data to the one or more heart state models and determine timing data for the sequence of heart states and a confidence value for the model fit; and an output to output one or both of a model fit indication dependent upon the confidence value and an indication of the timing data.

The electronic stethoscope system may comprise a system which is configured to be attached to an acoustic stethoscope, or the system may be built into a stethoscope. Such a stethoscope may be usable acoustically as well as electronically.

The acoustic signal capture device may comprise a suitable microphone or similar transducer. The electronic stethoscope system may include a processor and memory storing processor control code to perform the classification and model fitting functions. The processor and memory may be part of a stethoscope or these functions may be performed by partly or wholly by a remote device such as a smart phone. The output may comprise a visual indication on the stethoscope and/or an indication on a remote device such as a smart phone.

The electronic stethoscope system may incorporate further features as previously described.

The described system/method may be employed on human and animal acoustic heart signals. Captured sound data may be made available for processing and analysis via a wired or wireless connection to the stethoscope or stethoscope drum.

The described system/method may also be employed on other repetitive signals sensed from a human or animal body. These may be heart or other signals and may be, for example, electrically sensed rather than acoustically sensed signals.

BRIEF DESCRIPTION OF THE DRAWINGS

These and other aspects of the invention will now be further described by way of example only, with reference to the accompanying Figures, in which.

DETAILED DESCRIPTION OF PREFERRED EMBODIMENTS

Heart sound represented by a phonocardiogram or PCG may be captured and recorded while listening to the sound. A normal heart sound may be considered to have four states, the first heart sound (S1), systole, the second heart sound (S2) and diastole. An abnormal heart sound may have the same states but different types of sound during these states and/or different states.

Figure 1A:
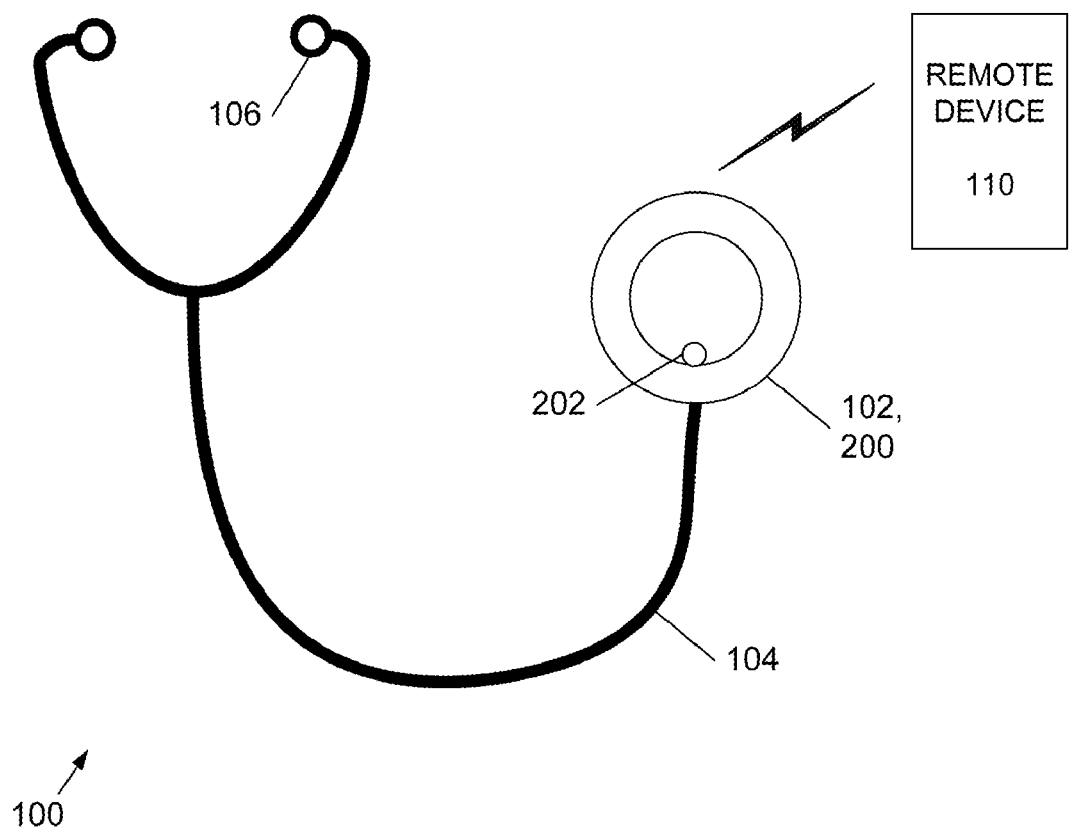
FIGS. 1a and 1b show a stethoscope incorporating an electronic stethoscope system, and a block diagram of the electronic stethoscope system.

Referring to FIG. 1a, in some implementations an electronic stethoscope 100 comprises a device 200 within or attachable to the chestpiece 102 of an acoustic stethoscope, or mounted at any other convenient location. The device uses a microphone or similar transducer to detect sounds from the chestpiece and converts these into an analogue electrical signal. The microphone may be located within the chestpiece or on the tubing 104 to the earpiece(s) 106, for example close to flush to an inner wall of the tubing so that it does not significantly obstruct or modify the acoustic characteristics of the tubing.

The signal from the microphone may be processed using a signal processing system to provide a local or remote output. The local output 202 may be a green/amber/red indicator to indicate, respectively, a normal heart sound, inadequate sound capture, and a heart sound which needs further investigation. The remote output may comprise a wireless transmission to another device 110 such as a smart phone or tablet.

Figure 1B:
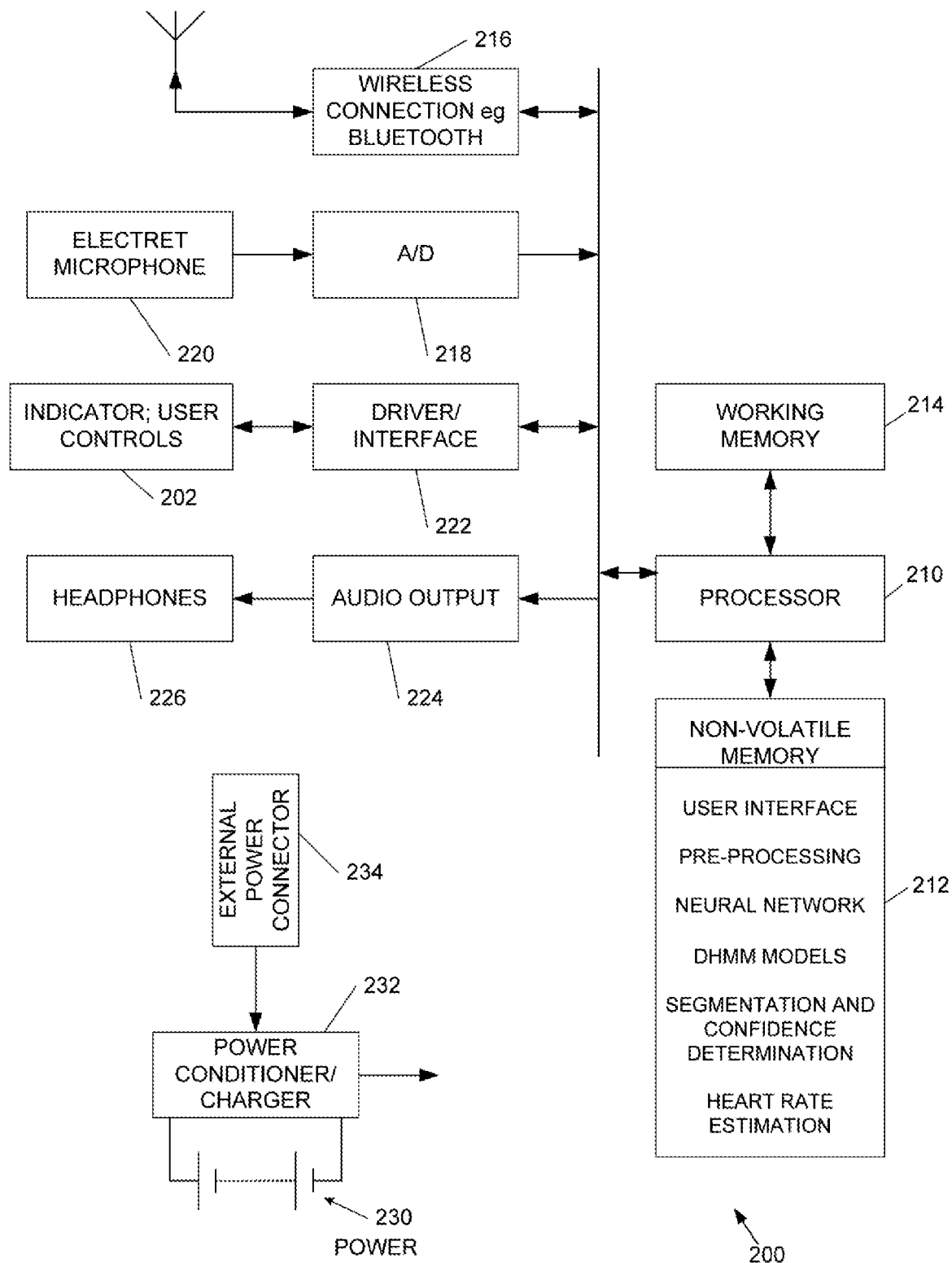

Referring to FIG. 1b, the device 200 comprises a processor 210 coupled to non-volatile memory 212 storing processor control code to implement functions of the device as described in detail later, and to working memory 214.

The non-volatile memory may store code and data to provide a user interface, to capture and pre-process heart sounds, a neural network to classify the heart sounds, duration-dependent hidden Markov models (DHMMs) to model heart states using the classified heart sounds, code to segment the captured heart sounds according to the models and to determine a confidence of the segmentation, and heart rate estimation code. The working memory may be used to store captured, unprocessed and/or heart sound data.

The processor is coupled to an electret microphone 220 via an analogue-to-digital converter, to capture the heart sounds; to a driver/interface 222 for indicator and user controls 202, for example an LED indicator and/or a text or graphical display, and a power on/start control; to an optional audio output circuit 224 which may provide a wired or wireless audio output to headphones 226 or the like; and to a wireless interface 216 such as a Bluetooth™ or WiFi™ interface.

A rechargeable battery 230 provides power to the system via a power conditioner 232 and an external power connector 234 for charging the battery.

Figure 2:
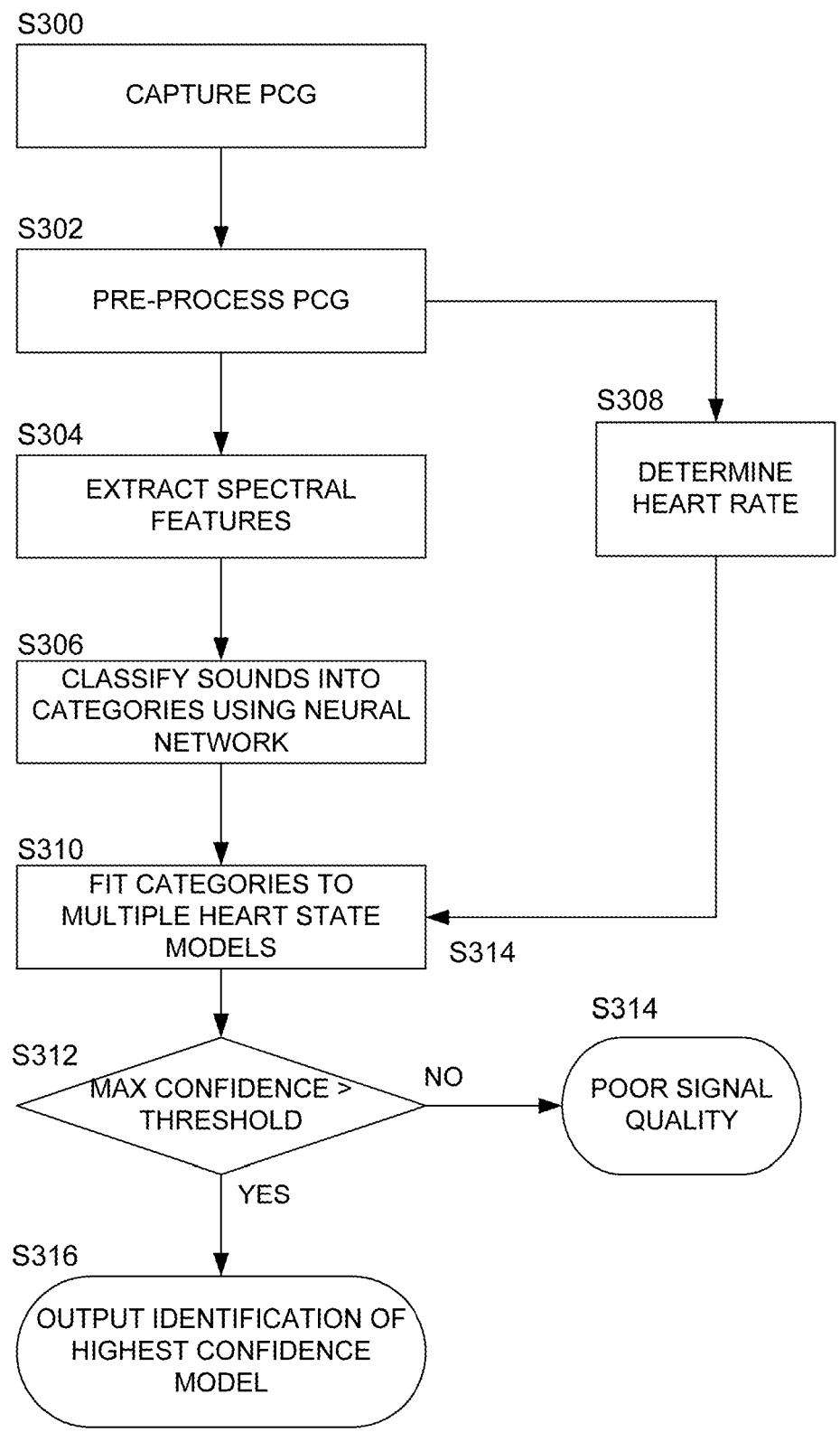
FIG. 2 shows steps in a method for processing acoustic heart signal data.

Referring to FIG. 2, this shows steps in a method for processing acoustic heart signal data, which may be implemented by the processor 210 of FIG. 1b.

At step (S300) the acoustic heart signal data (phonocardiogram) is captured by the microphone and converted to the digital domain by A/D 218 for pre-processing in the digital domain. (In other approaches analogue signal processing maybe employed).

The pre-processing (S302) may comprise filtering the signal, for example downsampling to 1000 Hz and then low-pass and high-pass filtering. Second order Butterworth filters may be employed with cut-off frequencies of 400 and 25 Hz respectively. The signal may be further filtered to reduce noise, friction spikes and the like.

Spectral features may then be extracted (S304), for representing the sound to the classifier. For example the signal may be low and high-pass filtered into 10 equally spaced frequency bins (e.g. bin 1 is 25-62.5 Hz, bin 2 is 62.5-100 Hz and so forth), and then the envelope, for example the homomorphic envelope, of each of these may then be found. This envelope may be downsampled to 50 Hz, thereby providing 10 features at each point in time. In addition the power spectral density of the signal time bin, for example in each 0.02 s time bin, may be found and then averaged into, e.g. 7, equally spaced frequency bins between 25 and 400 Hz. This gives a total of, in this example, 17 features at each point in time (sampled at 50 Hz). These features may then be individually normalised by subtracting the mean and dividing by the standard deviation across the whole length of the signal.

The time series of spectral features may then be classified (S306) by a neural network into a plurality of different sound classes or categories. The neural network may be a feedforward or a recurrent neural network; either of these may be a convolutional neural network.

For example the spectral features at each time instance may be used as the input to a feedforward neural network trained to distinguish between 3 classes, major heart sound (MHS), no sound (NS), and murmur (M). The neural network outputs a probability value for each of these three states given the features (observations). The neural network may be trained using labelled training data and error-backpropagation. In some implementations a number of neural networks may each be trained using slightly different data and then the networks may be used as an ensemble where each network gives an individual probability and the final probability is given by the average of all the individual probabilities from each network in the ensemble.

The heart rate is estimated (S308), for example using an autocorrelation function operating on an envelope such as a homomorphic envelope of the input signal after pre-processing. After finding the envelope and subtracting its mean, the autocorrelation is found. This is described in more detail later.

The sound categories are then fit to two independent heart state models (S310). Conveniently a duration-dependent hidden Markov model (DHMM) is used is to segment the heart sound signal into 4 states: S1, systole, S2, and diastole, but other state sequence models may be employed. The DHMM may be trained iteratively, using an expectation-maximization algorithm in which the observations are aligned to the states with maximum likelihood and then the model parameters updated, repeating until convergence.

A first model assumes that the heart sounds do not contain a murmur. For the states, q, {S1, systole, S2, diastole}={1, 2,3,4}, the pseudo-probabilities of these 4 states given the observations (O) at each instance in time are given by the outputs of the of the neural network as:

$P(q_1|O_t)=P(MHS)$ $P(q_2|O_t)=P(NS)$ $P(q_3|O_t)=P(MHS)$ $P(q_4|O_t)=P(NS)$.

This is explained in more detail later, but in general terms these probabilities are combined with state duration distributions in the model to determine a most likely heart state for each of a succession of times, according to the first model.

A second heart state model assumes that the heart sounds contain a systolic murmur. Thus the pseudo-probabilities of these 4 states given the observations are given by:

$P(q_1|O_t)=P(MHS)$ $P(q_2|O_t)=P(M)$ $P(q_3|O_t)=P(MHS)$ $P(q_4|O_t)=P(NS)$.

These are combined with state duration distributions in the second model to determine a most likely heart state for each of a succession of times, according to the second model.

The state duration distributions can be determined from training data; they may be assumed to be Gaussian. The heart rate estimation may be used to modify the mean duration of the systole and diastole states, again as described in detail later.

A confidence value for the model segmentation may be determined from a combination of the probability values from the neural network for each time instance, taking the probability value which corresponds to the state determined by the sequence model for the time.

In some implementations, rather than determining a confidence value the confidence value may be determined over just a few heartbeats, for example less than 10 heartbeats, in particular those for which the confidence value of the model segmentation is highest. In this way the techniques may be applied to the best available data and parts of the signal contaminated by speech or movement disregarded.

The maximum confidence value from the first and second model fits, determined as above, may be compared with a quality threshold (S312). If the confidence is less than this threshold the procedure may output an indication that the signal is of insufficiently high quality (S314). Otherwise the procedure outputs an indication of which model best fits the observations. This may comprise an indication that the heart sounds are normal or abnormal, depending upon which model fits the best.

The technique may be extended to add one or more further models, for example a model which includes a diastolic murmur. In this case the hierarchical order of confidence value magnitudes for the models may be employed to provide additional information as follows:

| Order of Confidence | | | | | | |
|---|---|---|---|---|---|---|
| Largest | NM | NM | SM | DM | SM | DM |
| Middle | SM | DM | NM | NM | DM | SM |
| Smallest | DM | SM | DM | SM | NM | NM |
| Identification | NM | NM | SM | DM | CM | CM |

Figure 3:
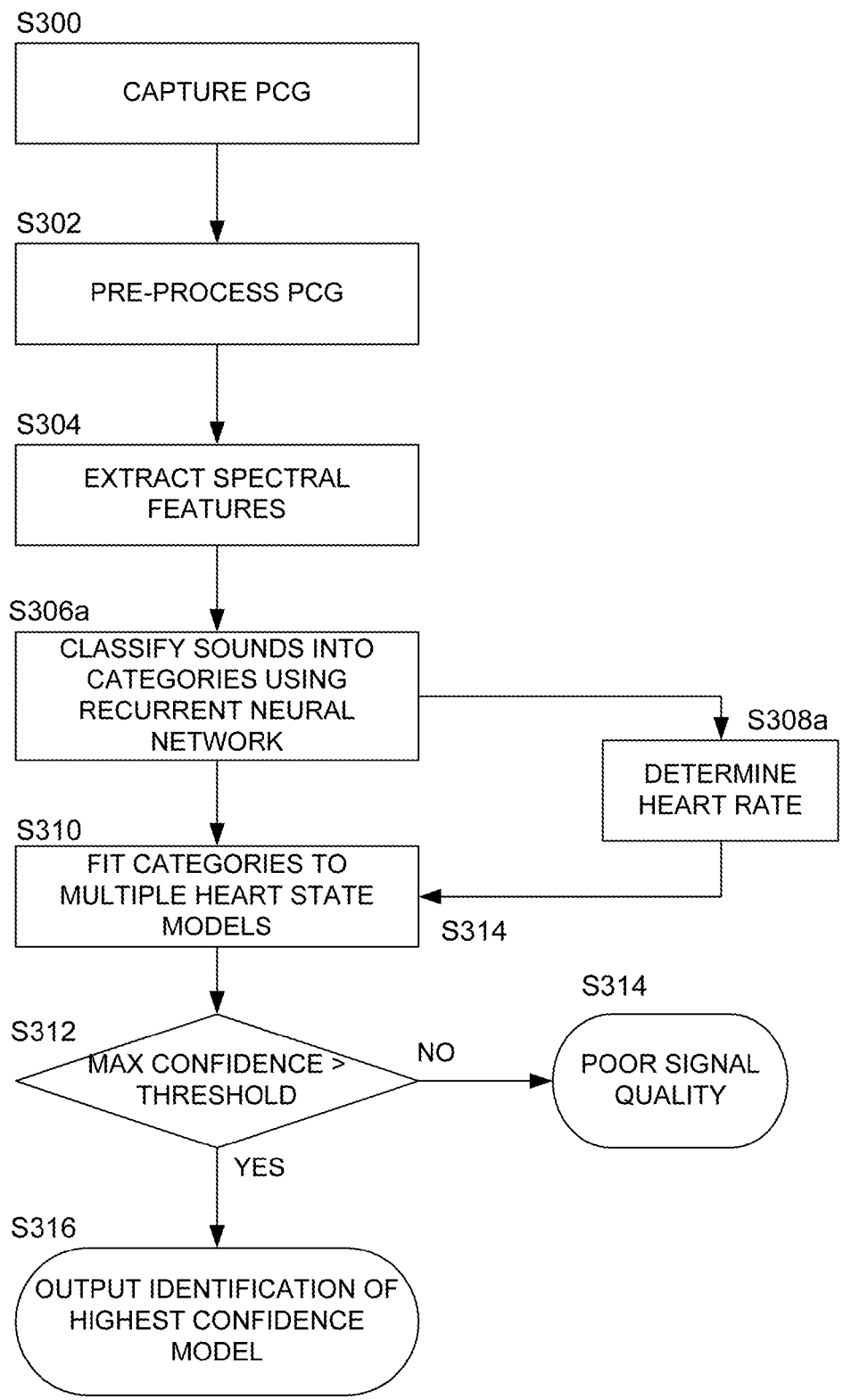
FIG. 3 shows a variant of the procedure of FIG. 2.

Key: NM = no murmur,
SM = systolic murmur,
DM = diastolic murmur,
CM = continuous murmur FIG. 3 shows a similar procedure to that of FIG. 2 where, in step S306a the neural network may be a recurrent neural network such as an LSTM (Long Short Term Memory) recurrent neural network. As before this neural network determines probabilities for the states of the state model, for example S1, systole, S2, and diastole, or some other set of states.

The heart rate is determined (S308a) from the probabilities from the neural network, again using an autocorrelation. It has been found experimentally that this can improve heart rate prediction.

This approach facilitates arrhythmia detection, such as the detection of missed beats, extra beats and other variations in heart beat rhythm such as a seemingly random non-periodic succession of beats. This may be facilitated by reducing the enforced periodicity of the model.

Murmur Intensity

The captured data may be processed to determine an estimate for the intensity of a murmur, for example according to the Levine grading scale.

In one implementation mel-frequency cepstral coefficients (MFCCs) are used to determine the intensity of a systolic murmur. For example to calculate the MFCCs a periodogram is found of each segment, with a 50% overlap either side. A Hamming window may be used to reduce spectral leakage. The periodogram gives values for the signal power in 21 evenly spaced frequency bins between 0 and 500. The periodogram is then filtered using a filter bank, in which frequencies, f, are equally spaced in the mel-scale:

$$Mel = 1125 \log\left(1 + \frac{f}{700}\right).$$

The MFCCs are obtained by taking the logarithm of each of the filtered periodograms, and then taking a discrete cosine transform:

$$MFCC(t, k) = \sum_{n=1}^{N_f} \log(P_{filt}(t, n)) \cos\left(\frac{k\pi}{N_f}(n - 0.5)\right),$$

where $MFCC(t,k)$ gives the $k^{th}$ cepstral feature of the $t^{th}$ time frame, $P_{filt}(t,n)$ is the filtered power at time frame t for the $n^{th}$ filter bank, and $N_f$ is the number of filter banks used. One example used 18 filterbanks equally spaced in the mel scale and calculated 6 cepstral coefficients at each point in time. A linear regression is trained on this, where the independent variables are the 6 cepstral coefficients at each time interval during systolic portions of the signal and the dependent variable is the murmur intensity.

This tends to bunch signals close to 2.5 murmur intensity to minimize mean square error. Each murmur intensity level is therefore considered to have a Gaussian distribution of regression outputs and the thresholds between each level are selected to be the average of their mean regression outputs. A murmur intensity level may thus be converted to a value on the Levine scale by comparison with the thresholds for the Levine grades. When a signal is processed using this scheme each point in time in systole is given a murmur intensity based on the output of the linear regression. This output is converted to a Levine grade by comparison with the thresholds and the final murmur intensity is given by the mean of all the individual systolic murmur intensities (Levine grades).

Example Implementation

There are now described further details of an example implementation using a DHMM.

An example DHMM segments a heart signal into four states (S1, systole, S2, and diastole) which are labelled 1 to 4, respectively, giving states $S=\{S_1,S_2,S_3,S_4\}$. For this example DHMM the instantaneous probability of changing to a new state from state j at the next time instance t is calculated as $$\delta_t(j) \approx P(O_1, O_2, \ldots, O_t, q_t=S_j, q_{t+1} \neq S_j | \lambda), \quad (1)$$

where O are observations or features of the PCG at a given time instance, $q_t$ defines the state at time t, and $\lambda$ are the model parameters.

In order to solve this, all possible combinations of Q at each time could be computed. As this is infeasibly large, the Viterbi algorithm is used. For a duration d, and a previous state i at time $t-d_j$, the probability that $q_t$ is the last time instance in state j is calculated as $$\delta_t(j, i, d) = \delta_{t-d}(i) a_{ij} p_j(d) \prod_{s=0}^{d-1} b_j(O_{t-s}), \quad (2)$$

where $\delta_{t-d}(i)$ is the probability that the previous state i ended at t−d. The constituent parts of this equation are described below.

Transition Probabilities $a_{ij}$

Since the states seen in the heart transition are observed in a predictable manner, the transition probabilities $a_{ij}$ may be set as $$\begin{array}{c} \quad\quad S1 \quad \text{systole} \quad S2 \quad \text{diastole} \\ \begin{array}{c} S1 \\ \text{systole} \\ S2 \\ \text{diastole} \end{array} \begin{pmatrix} 0 & 1 & 0 & 0 \\ 0 & 0 & 1 & 0 \\ 0 & 0 & 0 & 1 \\ 1 & 0 & 0 & 0 \end{pmatrix}, \end{array} \quad (3)$$

Duration Densities $p_j(d)$ $p_j(d)$ is the probability density function for the state duration d in state j, taken as a Gaussian distribution with mean, $d\mu_j$, and variance $d\sigma_j^2$. These durations are calculated using the estimated heart rate and systolic interval as in the example table below. The numbers in the example table are from training data. The algorithm used to estimate heart rate is described later.

| State | Mean/ms | Standard Deviation/ms |
|---|---|---|
| S1 | 128 | 21 |
| Systole | SI-128 | 25 |
| S2 | 105 | 18 |
| Diastole | TL-SI-105 | 50 |

The numbers are means and standard deviations of Gaussian distributions representing the duration densities $p_j(d)$; TL=total length of 1 heart cycle, SI=systolic interval.

Observation Probabilities $b_j(O_t)$ $b_j(O_{t-s})$ is the probability of an observation given the state at time t−s. One can calculate $b_j(O_t)$ as $$b_j(O_t) \equiv P(O_t \mid q_t = S_j) = \frac{P(q_t = S_j \mid O_t)P(O_t)}{P(S_j)}, \quad (4)$$

where $P(O_t)$ may be found from a multivariate normal distribution of the features over the training set, and $P(S_j)$ may be found from $\pi_j$, the initial state distribution, that may be set even for the four states such that $$\pi_j = 0.25 \ \forall j. \quad (5)$$

$P(q_t=S_j|O_t)$ is predicted from the output of a neural network that, for example, inputs features from across the frequency range 25-400 Hz at each 0.02 second.

The neural network has three outputs: major heart sound (MHS); no sound (NS); and murmur (M). Then, for a DHMM assuming a normal PCG:

$$P(q_t=S1|O_t)=P(MHS_t) \quad (6)$$

$$P(q_t=\text{systole}|O_t)=P(NS_t) \quad (7)$$

$$P(q_t=S2|O_t)=P(MHS_t) \quad (8)$$

$$P(q_t=\text{diastole}|O_t)=P(NS_t). \quad (9)$$

Then $b_{S1}(O_t)$, $b_{systole}(O_t)$, $b_{S2}(O_t)$, and $b_{diastole}(O_t)$ may be calculated from Bayes rule using equation (4).

For a DHMM assuming that there is a systolic murmur, the same probabilities for S1, S2, and diastole may be assumed but for systole $$P(q_t=\text{systole}|O_t)=P(M_t). \quad (10)$$

Viterbi Algorithm

In words Equation 2 says that the probability that $q_t$ is the final time instance in state j is the probability that $q_{t-d}$ is the final time instance in state i, multiplied by the transition state probability, multiplied by the duration density for state j, multiplied by the product of the probabilities of state j being generated by the outputs observed between t−d and t. The instantaneous probability of $q_t$ being the last time instance in state j at time t is maximised according to duration d and the previous state i $$\delta_t(j) = \max_d \max_{i \neq j}\left[\delta_{t-d}(i)a_{ij}p_j(d)\prod_{s=0}^{d-1}b_j(O_{t-s})\right] \quad (11)$$

Here, d is set to be from 1 to the length of an entire heart beat. The process is initialized using the initial state distribution $\pi_j$.

The duration and the previous state which maximize Equation 11 are stored for each t ($D_t(j)=d$ and $\psi_t(j)=i$). The final state is assigned as $$q_T^* = \underset{j}{\operatorname{argmax}}[\delta_T(j)]. \quad (12)$$

However, this only models accurately if the final point is at the end of a state, which will not often be the case. Thus the backtracking algorithm is then applied for T-1, T-2, ..., 2. First get the duration of $q_t^*$:

$$d^*=D_t(q_t^*). \quad (13)$$

All states are then assigned backwards from $q_t^*$ to all times up to d* before t $$q_{t-d^*}^*:t-1=q_t^*. \quad (14)$$

The end of the previous state is then assigned as $$q_{t-d^*-1}^*=\psi_t(q_t^*). \quad (15)$$

The time for the next iteration is then updated as $$t=t-d^*. \quad (16)$$

The process is then repeated until t=1.

A weaknesses with this algorithm is that it makes an approximation which assumes that the start and end points of the recording are the start and end points of a state, which will almost always not be the case. One way to address this weakness of the algorithm is to allow state durations to extend beyond start and end of the signal, while only considering observations from within the PCG. In other words for t≤T and t>1

$$\delta_t(j) = \max_d \max_{i \neq j}\left[\delta_{t-d}(i)a_{ij}p_j(d)\prod_{s=0}^{\min(d-1,t-1)}b_j(O_{t-s})\right], \quad (17)$$

such that one only considers observations back to t=1, and for t>T $$\delta_t(j) = \max_d \max_{i \neq j}\left[\delta_{t-d}(i)a_{ij}p_j(d)\prod_{s=t-T}^{\max(d-1,t-T+1)}b_j(O_{t-s})\right], \quad (18)$$

such that one only considers observations backwards from T.

This algorithm allocates most likely labels of S1, systole, S2, and diastole at each time instance for the whole PCG as $q_t^*$.

The confidence of each model is given as the mean posterior probability of the found state sequence given the observations:

$$C_{DHMM} = \left(\prod_{t=1}^{T} P(q_t^* \mid O_t)\right)^{\frac{1}{T}}. \quad (19)$$

In equation (19) $P(q_t^*|O_t)$ is given by the output of the neural network at time instance t for the identified optimal state $q_t^*$. For example if for the normal model at time t $q_t^*=S1$ then $P(q_t^*|O_t)=P(MHS_t)$ for the normal model, and if for the second model at time t $q_t^*$=systole then $P(q_t^*|O_t)=P(M_t)$, and so forth.

When running parallel models this confidence value can be used to determine whether a good segmentation has been found, and if so whether a murmur is present.

Heart-Rate Estimation

The heart rate and systolic interval may be found by detecting peaks of an autocorrelation function applied to the homomorphic envelope, or applied to the outputs of the neural network for improved heart rate prediction. The scheme described below is similar for both approaches.

Figure 4A:
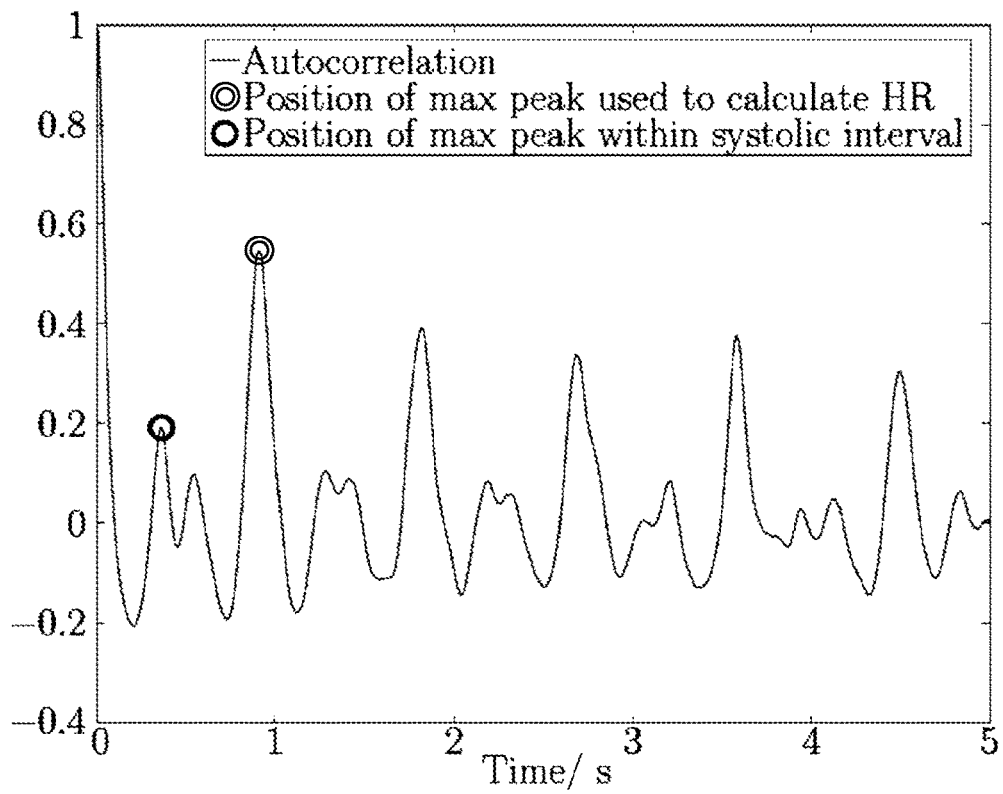
FIGS. 4a and 4b show, respectively, an example autocorrelation applied to the homomorphic envelope of a captured heart sound, and an error condition.
Figure 4B:
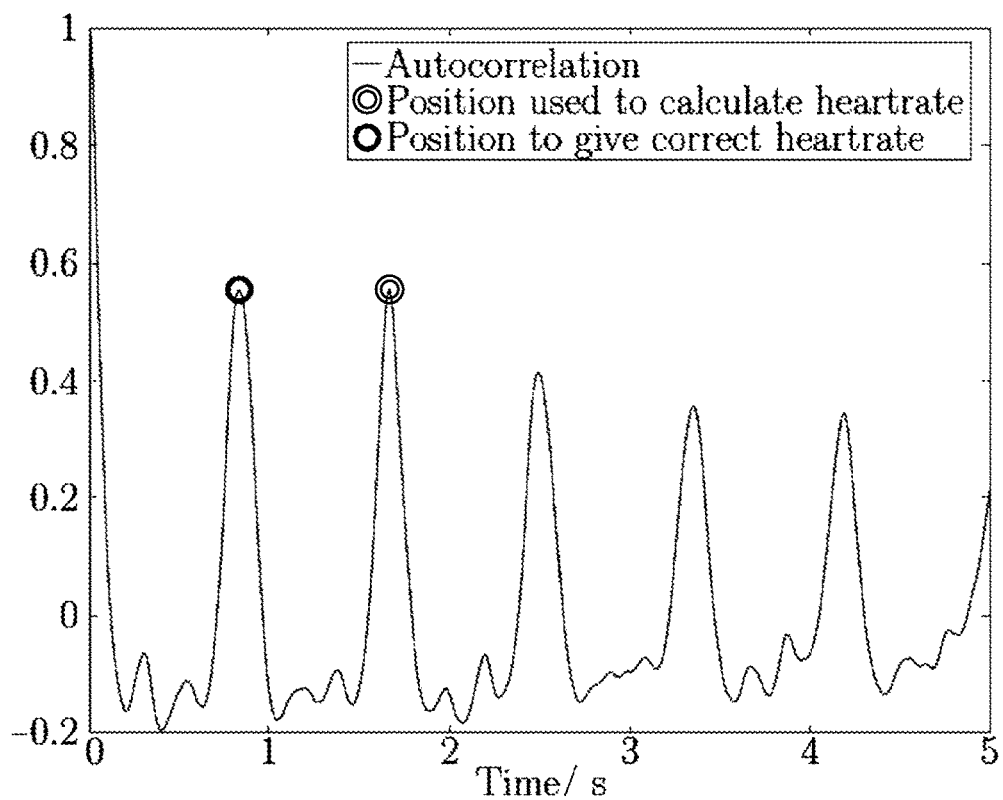

Thus FIG. 4a shows an example autocorrelation applied to the homomorphic envelope, and the peaks used to determine heart rate and systolic time interval. The heart beat duration may be determined from the time interval from zero to the highest peak lying between 500 and 2000 ms in the autocorrelation. The systolic time duration may then be determined from the time interval from zero to the highest peak lying between 200 ms and half the heart cycle duration in the autocorrelation This approach can result in segmentation errors when the algorithm picks the wrong peak in the autocorrelation function, resulting in a heart rate estimate of half the true value. FIG. 4b shows an example in which the highest peak gives a heart rate of 36 bpm but a very similar sized peak gives the correct heart rate of 72 bpm.

In order to address this a technique is employed which takes into account both the magnitude of the autocorrelation and the prior probability of the heart rate. Mathematically, this may be expressed as $$t_{hr}^* = \operatorname*{argmax}_t [Y(t) p_{hr}(t)^{n_{hr}}] \quad (20)$$

where $t_{hr}^*$ is the chosen point in time, Y (t) is the height of auto-correlation (compressed from −1 to 1, to, 0 to 1), $p_{hr}(t)$ is an estimate of the probability of the total heartbeat length (drawn from a normal distribution of all the training data), and $n_{hr}$ is a parameter to be tuned which represents the relative importance of the two components. For example, a lower $n_{hr}$ gives the auto-correlation a higher weighting than the prior probability of the heartbeat duration. $p_{hr}(t)$ may be taken as a Gaussian distribution across the training data with, for example a mean of 890 ms and a standard deviation of 175 ms. It is also helpful to increase the upper limit of heartrate from 120 to 150 bpm, so that the range of t considered is from 400 ms to 2000 ms. In one implementation $n_{hr}$ was chosen as 0.02 to minimize errors in the training set.

A similar scheme may be applied to the estimation of the systolic interval:

$$t_{si}^* = \operatorname*{argmax}_t [Y(t) p_{si}(t)^{n_{si}}] \quad (21)$$

where $t_{si}^*$ is the chosen point in time, $p_{si}(t)$ is an estimate of the probability of the systolic interval (drawn from a normal distribution of all the training data), and $n_{si}$ is a parameter to be tuned which represents the relative importance of the two components. The range of t considered for the systolic interval may be from 200 ms to half the total heartbeat length. $p_{si}(t)$ may be taken as a Gaussian distribution whose mean is correlated with the total heartbeat duration. For example in one dataset a linear regression on the training data gives the mean of $p_{si}(t)$ as $$\mu_{si} = 161.9 + 0.1883 t_{hr}, \quad (22)$$

where in $t_{hr}$ the total heartbeat length in milliseconds. The standard deviation is taken as 31.2 (half of the 95% confidence interval). In one implementation $n_{si}=0.02$ was chosen as to minimize the number of errors in the training set.

Neural Network Sequence Modelling

In another approach live or recorded heart sound data is resampled to 1 kHz and normalized to a −1 to 1 range. The signals are then band-pass filtered between 25-400 Hz using an order 2 Butterworth filter. Spikes in each recordings are removed by looking for large deviations from the median.

A variety of time frequency features are extracted from the signal:

Homomorphic envelopes: The signal is bandpass filtered using 10 different frequency bands evenly spaced between 25 and 400 Hz and the homomorphic envelope of each bandpass filtered signal is calculated as a feature.

Mel-frequency cepstral coefficients (MFCCs): MFCCs are calculated using 20 filter banks and 40 frequency bins; just the first 12 features are kept.

Power spectral density bands: The spectrogram of the signal is determined using a window size of 25 and an overlap of 50%, with frequencies evaluated in 1 Hz intervals between 1 and 500 Hz. The frequency response of the signal is averaged (keeping the time dimension) in 7 bands evenly spaced between 25 and 400 Hz. Each of the features is then resampled to 50 Hz to reduce computation. The means and standard deviations of the entire dataset are saved to normalize the feature distribution during training and testing.

A recurrent neural network (RNN) is trained to classify each time step of the sequence, represented by a vector of the features, into a particular label. The labels denote the type of heart sound associated with a heart state (S1, systole, S2, diastole, murmur). Thus the RNN may be trained to classify heart sounds into one of these five categories.

Figure 5:
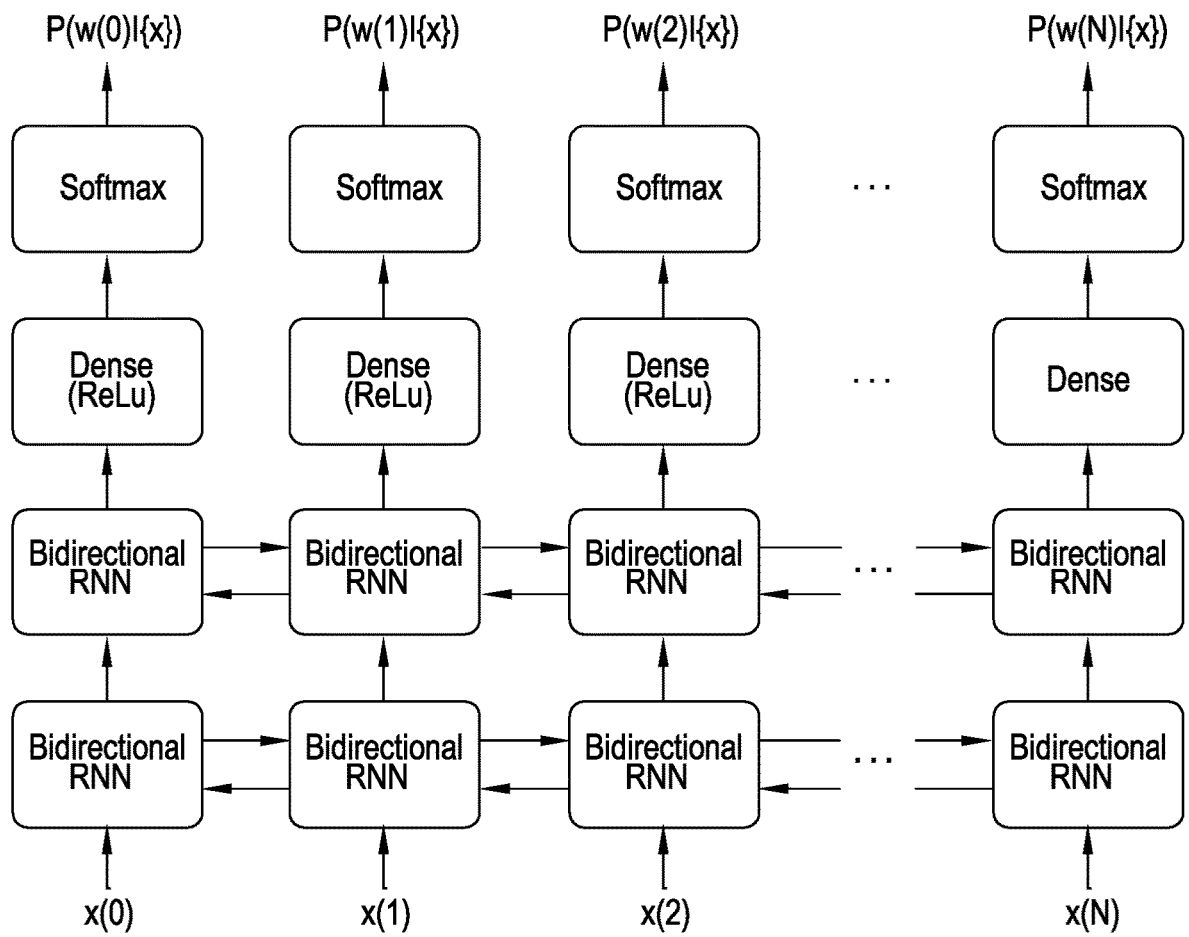
FIG. 5 shows an example neural network for use in a system for classifying acoustic heart data as normal or abnormal.

One example recurrent neural network is shown in FIG. 5, comprising a sequence-to-sequence RNN which classifies each feature vector x(t) as a particular heart sound label w(t). The example RNN of FIG. 5 comprises two initial layers of bidirectional gated recurrent units (biGRUs). Fully-connected dense neural network layers are then applied at each time instance, to transform each biGRU output into a 5-dimensional vector, corresponding to the five types of heart sound. A softmax function is applied to each vector to calculate the probability of each label at each time step. The actual label at each time instant is chosen by picking the label with largest probability.

A bidirectional RNN may be applied to captured and stored heart sound data; a unidirectional RNN may be used to process heart sound data in real time.

Murmur classification: The neural network of FIG. 5 provides a posterior label probability for each time step. The confidence, C, may be calculated by summing the probabilities of the chosen labels and taking a mean:

$$C = \frac{1}{T} \prod_{t=0}^{T-1} \left( \max_i \{P(w_i(t)|\{x\})\} \right)$$

where T represents the duration of the heart sound data and $$\max_i \{P(w_i(t)|\{x\})\}$$

is the probability of the most likely label amongst the i labels.

To determine if a systolic murmur is present two versions of the confidence measure are determined. In a first determination, corresponding to a healthy cardiac cycle, the labels are constrained to not contain the murmur label, for example by selecting the label with the maximum probability from the four labels associated with a healthy cardiac cycle. In a second determination, corresponding to an abnormal cardiac cycle, the labels are constrained to use the murmur label instead of the systolic label.

If the confidence in the murmur segmentation (abnormal cardiac cycle) is greater than the confidence in the healthy segmentation (healthy cardiac cycle), the presence of a murmur is determined. However, if the confidence in both classifications is low, the signal may be rejected as poor quality.

Figure 6:
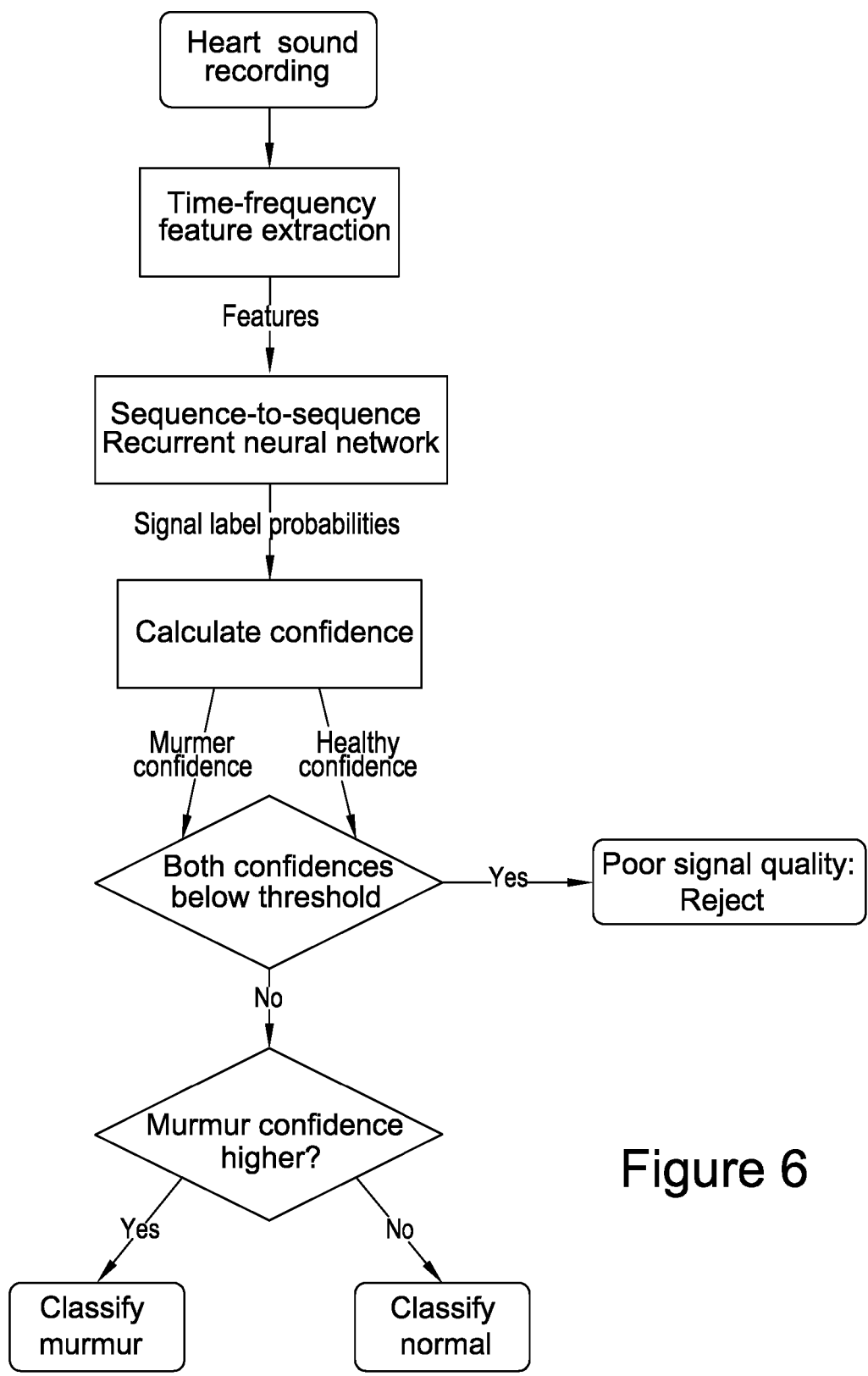
FIG. 6 shows a procedure for automatic heart murmur detection using the neural network of FIG. 5.

FIG. 6 shows a flow diagram of a procedure as described above which may be implemented in software for automatic heart murmur determination.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A method of processing acoustic heart signal data, the method comprising:
    capturing time series acoustic heart signal data from a patient, the time series acoustic heart signal data representing the sound of the patient's heart;
    classifying the time series acoustic heart signal data into a plurality of heart sound categories to provide time series sound category data, wherein the time series sound category data comprises, for each of a plurality of time intervals, category probability data representing a probability of the acoustic heart signal for the time interval falling into each of the heart sound categories;
    fitting the time series sound category data to a heart state model having a sequence of heart states with associated heart sounds corresponding to the heart sound categories and adjustable durations of the states, to determine timings of the sequence of states;
    determining, from the timings of the sequence of states and corresponding category probability data, a confidence value for the model fit; and
    outputting one or both of a model fit indication dependent upon the confidence value, and data identifying timings of the sequence of states.

2. A method as claimed in claim 1 wherein the heart state model comprises a probability distribution for the duration of each heart state, wherein each heart state is associated with one of the heart sound categories, and wherein fitting the time series sound category data to the heart state model comprises combining, for each of a succession of time intervals, the category probability data and the probability distribution for the duration of each state to provide sequence data identifying a most likely state for each of the time intervals.

3. A method as claimed in claim 1 wherein each heart state is associated with one of the heart sound categories, wherein the timings of the sequence of states define a most likely heart state for each of the succession of the time intervals, and wherein determining the confidence value for the model fit comprises combining, for a succession of the time intervals, the category probability data for the heart sound category associated with the most likely heart state for each time interval.

4. A method as claimed in claim 1 further comprising determining a heart rate using the time series acoustic heart signal data, and adapting the probability distributions for the durations of one or more of the states to the determined heart rate.

5. A method as claimed in claim 1 comprising fitting the time series sound category data to first and second heart state models having different sequences of associated heart sounds and determining respective confidence values for the model fits, wherein the first heart state model represents a normal heart and the second heart state model represents an abnormal heart; and wherein outputting the model fit indication comprises outputting an indication of which heart state model is a best fit to the captured time series acoustic heart signal data.

6. A method as claimed in claim 5 wherein the second heart state model comprises a model of a heart with a systolic and/or diastolic murmur.

7. A method as claimed in claim 6 wherein the second model includes a systolic and/or diastolic heart state associated with a heart sound comprising a murmur; the method further comprising determining a measure of an intensity of the murmur.

8. A method as claimed in claim 7 wherein determining a measure of an intensity of the murmur comprises: determining, for each of a plurality of times during the murmur, a set coefficients characterising the time series acoustic heart signal data over a plurality of frequency bands; mapping, for each of the plurality of times, the set of coefficients to a murmur intensity value; and combining the murmur intensity values for the plurality of times to determine a measure of the intensity of the murmur.

9. A method as claimed in claim 1 wherein the heart sound categories comprise at least a major heart sound, no sound, and a murmur.

10. A method as claimed in claim 1 wherein the heart states comprise S1, systole, S2 and diastole heart states.

11. A method as claimed in claim 1 further comprising processing the acoustic heart signal to provide an acoustic data sequence comprising a sequence of data elements representing the acoustic heart signal; and wherein classifying the time series acoustic heart signal data comprises classifying the acoustic data sequence using a neural network.

12. A method of processing an acoustic heart signal, the method comprising:
    capturing an acoustic heart signal from a patient;
    processing the acoustic heart signal to provide an acoustic data sequence comprising a sequence of data elements representing the acoustic heart signal;
    classifying the sequence of data elements using a neural network to provide a sequence of acoustic data category classifications and associated probabilities, each acoustic data category classification classifying one or more of the data elements into one of a plurality of acoustic heart data categories with an associated probability;
    processing the sequence of acoustic data category classifications and associated probabilities using one or more sequence models, where each sequence model represents the likelihood of a sequence of heart sounds represented by the acoustic data category classifications and associated probabilities, wherein the processing identifies a most likely sequence of the heart sounds; and outputting data identifying the most likely sequence of the heart sounds.

13. A method as claimed in claim 12 wherein the processing using one or more sequence models comprises processing using a plurality of sequence models and selecting a most likely model from the plurality of sequence models to identify the most likely sequence of the heart sounds.

14. A method as claimed in claim 12 further comprising estimating a heart rate from the acoustic heart signal, and using a timing of the estimated heart rate to adjust the associated probabilities for the acoustic data classifications to identify a most likely sequence of the heart sounds.

15. A method as claimed in claim 12 further comprising determining a confidence level for the most likely sequence of the heart sounds, and outputting, with the data identifying the most likely sequence of the heart sounds, an indication of whether a threshold confidence level is met by the most likely sequence of the heart sounds.

16. A method as claimed in claim 12 wherein outputting data identifying the most likely sequence of the heart sounds comprises outputting data identifying whether the patient has an abnormal heart sound.

17. A method as claimed in claim 12 wherein the one or more sequence models comprise at least a first sequence model of a normal heart and a second sequence model of an abnormal heart.

18. A method of processing acoustic heart signal data, the method comprising:

capturing time series acoustic heart signal data from a patient, the time series acoustic heart signal data representing the sound of the patient's heart;

extracting acoustic features from the time series acoustic heart signal data to provide time series acoustic feature data;

classifying the time series acoustic feature data using each of at least two heart models, a first heart model representing a normal heart and a second heart model represents a heart with a heart murmur; and determining which of the first model and the second model best fits the acoustic heart signal data; and outputting data indicating whether or not the patient's heart has a heart murmur when the second heart model fits the acoustic heart signal data better than the first model.

19. One or more non-transitory computer readable storage medium carrying processor control code to implement the method of claim 1.

20. An electronic stethoscope system comprising the one or more non-volatile data carriers of claim 19.

21. An electronic stethoscope system, the system comprising:

an acoustic signal capture device to capture time series acoustic heart signal data from a patient;

a neural network to classify the time series acoustic heart signal data into a plurality of heart sound categories to provide time series sound category data, wherein the time series sound category data comprises, for each of a succession of time intervals, category probability data representing a probability of the acoustic heart signal for the time interval falling into each of the heart sound categories;

one or more heart state models each having a sequence of heart states;

a system to fit the time series sound category data to the one or more heart state models and determine timing data for the sequence of heart states and a confidence value for the model fit; and an output to output one or both of a model fit indication dependent upon the confidence value and an indication of the timing data.

* * * * *